(12) United States Patent
Bartorelli et al.

(10) Patent No.: US 6,207,200 B1
(45) Date of Patent: Mar. 27, 2001

(54) USE OF PROTEINS AS ANTI-RETROVIRAL AGENTS

(75) Inventors: Alberto Bartorelli; Carlo De Giuli Morghen, both of Milan (IT)

(73) Assignee: Zetesis S.p.A., Milan (IT)

( * ) Notice: Subject to any disclaimer, the term of this patent is extended or adjusted under 35 U.S.C. 154(b) by 0 days.

(21) Appl. No.: 09/254,722

(22) PCT Filed: Sep. 11, 1997

(86) PCT No.: PCT/EP97/04966

§ 371 Date: Apr. 6, 1999

§ 102(e) Date: Apr. 6, 1999

(87) PCT Pub. No.: WO98/11137

PCT Pub. Date: Mar. 19, 1998

(30) Foreign Application Priority Data

Sep. 13, 1996 (IT) ............................................. MI96A1884

(51) Int. Cl.[7] ...................... A61K 35/407; A61K 38/04; A61K 38/17

(52) U.S. Cl. ............................ 424/553; 424/94.1; 514/2; 514/12; 514/21

(58) Field of Search .................................. 514/12, 2, 21; 424/94.1, 553

(56) References Cited

U.S. PATENT DOCUMENTS 5,792,744 * 9/1998 Ronchi et al. ........................... 514/2
5,824,640 * 10/1998 Bartorelli et al. ...................... 514/12

FOREIGN PATENT DOCUMENTS

| 92/10197 | * | 6/1992 | (WO) | ............................. A61K/35/00 |
| 96/02567 | * | 2/1996 | (WO) | ............................. C07K/14/47 |
| 97/30154 | | 8/1997 | (WO) . | |

OTHER PUBLICATIONS

Oka et al. Journal of Biological Chemistry vol. 270 No. 50 pp. 30060–30067, Oct. 1995.*
Shah et al. Journal of Cell Science vol. 108 pp. 985–1002, 1995.*
Levy–Favatier et al. Eur. J. Biochem vol. 212 665–673, 1993.*
Callard et al. The Cytokine FactsBook pp. 39–41, 1994.*
Ho, David D. Viral Counts Count in HIV Infection; Science, vol. 272 pp. 1124–1125, May, 1996.*
Mellors et al. Prognosis in HIV–1 Infection Predicted by the Quantity of Virus in Plasma; Science, vol. 272 pp. 1167–1170, May 1996.*
FEBS Letters, vol. 393, No. 1–2, Sep. 16, 1996, "The Primary Structure of UK114 Tumor Antigen", F. Ceciliani et al, pp. 147–150.

* cited by examiner

*Primary Examiner*—Jon P. Weber
*Assistant Examiner*—Patricia Patten

(57) ABSTRACT

The present invention relates to the discovery that a protein, having a molecular weight of about 14 Kd, extracted with perchloric acid from animal organs such as goat liver, has anti-retroviral activity, and may be used in the treatment of Human Immunodeficiency Virus.

1 Claim, No Drawings

USE OF PROTEINS AS ANTI-RETROVIRAL AGENTS

This application is a 371 of PCT/EP97/04966, filed Sep. 11, 1997.

The present invention relates to the use of a protein of a molecular weight of about 14 Kda, extracted from animal organs, for the preparation of medicaments with anti-retroviral activity, in particular against HIV, the Human Immunodeficiency Virus.

The therapeutical problems related with infection of the HIV retrovirus are well known. In particular, the increasing diffusion of the infection and the severity of the disease caused by the virus, known as Acquired Immunodeficiency Syndrome or AIDS, induced great research efforts which are producing promising results in terms of possibility of control and therapy of the infection. For example, the protease inhibitors have recently joined the reverse transcriptase inhibitors, such as azidothymidine. Moreover, the researches for the development of prophylactic or therapeutical vaccines continue, although they have, up to now, been hampered by the remarkable capability of HIV to escape the immune system thanks to continuous mutations.

On the other hand, the main problem with pharmacological therapy lies in the onset of resistance to the medicaments used.

Recently it has been found that proteins extractable with perchloric acid from mammalian organs, described in WO 92/10197, are capable of inhibiting the in vitro viral replication, inducing an immune and cytotoxic response to lymphocytes infected by the virus in patients affected by AIDS. The protein having the following sequence (SEQ. ID NO: 1) showed to be particularly active:

reported above, isolated from goat liver, have been described by a number of authors (for example: Levy-Favatier et al., in Eur. J. Biochem. 1903, 212(3), 665–73) which desumed the sequence from the cDNA recovered from different animal species, in particular from rat liver.

The anti-HIV activity elicited by the p14 protein has been demonstrated using sera dotained from animals or humans previously immunized with p14. For this purpose, the protein was administered subcutaneously at doses of 1–2 mg every seven days for 4–6 weeks, until reaching a significant anti-p14 antibody titre. The resulting sera were incubated on E-line cells (a derivative of human T-lymphocytes cell line HuT78 chronically infected with the HIV-1$_{SF2}$ virus) or normal, non-infected, HuT78 cells.

Said cells were mixed in a 1:1000 ratio (1 cell E-line producing virus each 1000 normal cells Hut78) plated on 24-well plates at a concentration of 1×10$^5$ cells/well in 1 ml of RPMI 1640 culture medium containing 5% of foetal bovine serum and antibiotics. Each well was then added with the test serum at a 5% final concentration so as to reach a 10% final total serum concentration. Control samples received the RPMI 1640 culture medium containing 5% of foetal bovine serum and 5% of normal human serum.

As a positive control, rabbit anti HIV-1 hyperimmune sera were used, which were able to inhibit the viral infectivity by about 3 log.

After 5 days of incubation, the culture media were centrifuged and quantification of the produced virus was done by the HIV-1 p24 core antigen capture assay.

The tested sera have shown high inhibition percentage, suggesting a therapeutical activity of p14 protein, which could be used as immunogenic antigen. Antibodies raised against this protein could be used as well.

Such an activity has in fact been confirmed, although up to now in a limited number of cases, also in vivo in HIV-positive and in clinically ill AIDS patients.

```
Met Ser Glu Asn Ser Glu Glu Pro Val Gly Glu Ala Lys Ala
1               5                   10

Pro Ala Ala Ile Gly Pro Tyr Ser Gln Ala Val Leu Val Asp
15                  20                  25

Arg Thr Ile Tyr Ile Ser Gly Gln Leu Gly Met Asp Pro Ala
    30              35                  40

Ser Gly Gln Leu Val Pro Gly Gly Val Val Glu Glu Ala Lys
        45              50                  55

Gln Ala Leu Thr Asn Ile Gly Glu Ile Leu Lys Ala Ala Gly
            60              65                      70

Cys Asp Phe Thr Asn Val Val Lys Ala Thr Val Leu Leu Ala
                75                  80

Asp Ile Asn Asp Phe Ser Ala Val Asn Asp Val Tyr Lys Gln
85                  90                  95

Tyr Phe Gln Ser Ser Phe Pro Ala Arg Ala Ala Tyr Gln Val
    100                 105                 110

Ala Ala Leu Pro Lys Gly Gly Arg Val Glu Ile Glu Ala Ile
        115                 120                     125

Ala Val Gln Gly Pro Leu Thr Thr Ala Ser Val
            130                 135
```

Said protein, in the following referred to as p14, having molecular weight of about 14 Kd, can be obtained by perchloric extraction of mammals livers and subsequent purification by dialysis, HPLC and hydrophobic exchange chromatography, according to the protocol described in WO96/02567.

The invention also relates to the use of proteins having at least an 80% (preferably 90%) homology with the sequence reported above. Proteins with sequences very similar to that Six patients were treated subcutaneously for four weeks with 1 mg of p14 every 7 days.

After each injection and before the treatment, the following parameters were measured:

T4/T8 ratio;

number of rosette receptors;

total lymphocytes' number;

T4 increase;

cells' number;

granulocytes' number.

At the end of the treatment the serological parameters tended to improve and the hematological pattern showed a normalization.

Some years after the treatment, the patients are still alive and their conditions quite satisfactory.

The p14 protein can be administered, according to the invention, in the form of suitable formulations, usually injectable, optionally containing conventional adjuvants such as aluminium hydroxide, polysaccharides, carrier proteins etc.

The procedure of administration (doses, frequency of administration, etc.) will be determined according to the circumstances, depending on different factors such as conditions of the patient, stage of the disease, hematological and serological parameters. Anti-p14 antibody titre can be used for monitoring the therapy, together with the common parameters used for the immunological functionality. Generally, a subcutaneous injection of a protein dose ranging from 0.1 to 10 mg, (preferably from 1 to 2 mg), can be administered every week for 3–6 weeks or, anyhow, until an objective therapeutical response is obtained.

What is claimed is:

1. A method of improving serological and hematological parameters in a subject infected with Human Immunodeficiency Virus Type I, comprising administering to a subject in need of such treatment a therapeutically effective amount of a protein comprising the amino acid sequence of SEQ ID NO:1.

* * * * *

SEQUENCE LISTING (1) GENERAL INFORMATION:

(iii) NUMBER OF SEQUENCES: 1

(2) INFORMATION FOR SEQ ID NO: 1:

(i) SEQUENCE CHARACTERISTICS:
      (A) LENGTH: 137 amino acids
      (B) TYPE: amino acid
      (C) STRANDEDNESS:
      (D) TOPOLOGY: linear (ii) MOLECULE TYPE: protein (iii) HYPOTHETICAL: NO (iv) ANTI-SENSE: NO (xi) SEQUENCE DESCRIPTION: SEQ ID NO: 1:

```
Met Ser Glu Asn Ser Glu Glu Pro Val Gly Glu Ala Lys Ala
1               5                   10

Pro Ala Ala Ile Gly Pro Tyr Ser Gln Ala Val Leu Val Asp
15                  20                  25

Arg Thr Ile Tyr Ile Ser Gly Gln Leu Gly Met Asp Pro Ala
        30                  35                  40

Ser Gly Gln Leu Val Pro Gly Gly Val Val Glu Glu Ala Lys
            45                  50                  55

Gln Ala Leu Thr Asn Ile Gly Glu Ile Leu Lys Ala Ala Gly
                60                  65                  70

Cys Asp Phe Thr Asn Val Val Lys Ala Thr Val Leu Leu Ala
                    75                  80

Asp Ile Asn Asp Phe Ser Ala Val Asn Asp Val Tyr Lys Gln
85                  90                  95

Tyr Phe Gln Ser Ser Phe Pro Ala Arg Ala Ala Tyr Gln Val
        100                 105                 110

Ala Ala Leu Pro Lys Gly Gly Arg Val Glu Ile Glu Ala Ile
            115                 120                 125

Ala Val Gln Gly Pro Leu Thr Thr Ala Ser Val
                130                 135
```